(12) United States Patent
Lee et al.

(10) Patent No.: US 9,688,620 B2
(45) Date of Patent: *Jun. 27, 2017

(54) METHODS FOR TREATING FIBROMYALGIA SYNDROME

(71) Applicant: SK Biopharmaceuticals Co., Ltd., Seoul (KR)

(72) Inventors: Sung James Lee, Montville, NJ (US); Susan Marie Melnick, Parsippany, NJ (US)

(73) Assignee: SK Biopharmaceuticals Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/495,416

(22) Filed: Sep. 24, 2014

(65) Prior Publication Data

US 2015/0011625 A1  Jan. 8, 2015

Related U.S. Application Data

(63) Continuation of application No. 13/508,145, filed as application No. PCT/KR2010/007603 on Nov. 1, 2010, now Pat. No. 8,927,602.

(60) Provisional application No. 61/258,672, filed on Nov. 6, 2009.

(51) Int. Cl.
| | |
|---|---|
| *C07C 271/08* | (2006.01) |
| *A61K 31/137* | (2006.01) |
| *A61K 31/223* | (2006.01) |
| *A61K 31/27* | (2006.01) |

(52) U.S. Cl.
CPC .......... *C07C 271/08* (2013.01); *A61K 31/137* (2013.01); *A61K 31/223* (2013.01); *A61K 31/27* (2013.01)

(58) Field of Classification Search
None
See application file for complete search history.

(56) References Cited

U.S. PATENT DOCUMENTS

| | | | |
|---|---|---|---|
| 5,705,640 A | 1/1998 | Choi et al. | |
| 5,756,817 A | 5/1998 | Choi et al. | |
| 5,955,499 A | 9/1999 | Choi et al. | |
| 6,002,009 A | 12/1999 | Cereda et al. | |
| 6,140,532 A | 10/2000 | Choi et al. | |
| 7,642,261 B2 | 1/2010 | Bartoszyk et al. | |
| 8,232,315 B2 | 7/2012 | Lee et al. | |
| 8,440,715 B2 * | 5/2013 | Ahnaou et al. | 514/478 |
| 8,552,060 B2 | 10/2013 | Palumbo et al. | |
| 8,623,913 B2 * | 1/2014 | Melnick et al. | 514/489 |
| 8,741,950 B2 * | 6/2014 | Khayrallah et al. | 514/478 |
| 8,877,806 B2 * | 11/2014 | Ahnaou et al. | 514/478 |
| 8,927,602 B2 * | 1/2015 | Lee et al. | 514/476 |
| 2001/0034320 A1 | 10/2001 | Brecht et al. | |
| 2002/0151585 A1 | 10/2002 | Plata-Salaman et al. | |
| 2002/0156127 A1 | 10/2002 | Plata-Salaman et al. | |
| 2003/0153612 A1 | 8/2003 | Sethi | |
| 2004/0115263 A1 | 6/2004 | Robertson et al. | |
| 2005/0080268 A1 | 4/2005 | Choi et al. | |
| 2006/0258718 A1 | 11/2006 | Choi et al. | |
| 2007/0123519 A1 | 5/2007 | Abarghaz et al. | |
| 2007/0197657 A1 | 8/2007 | Beyreuther et al. | |
| 2008/0039529 A1 | 2/2008 | Sporn | |
| 2008/0090902 A1 | 4/2008 | Pandey et al. | |
| 2010/0093801 A1 | 4/2010 | Chung et al. | |
| 2012/0245226 A1 | 9/2012 | Lee et al. | |
| 2012/0252892 A1 | 10/2012 | Lee et al. | |
| 2013/0137764 A1 | 5/2013 | Ahnaou et al. | |

FOREIGN PATENT DOCUMENTS

| | | |
|---|---|---|
| EP | 0633023 | 1/1995 |
| WO | WO 95/27490 A1 | 10/1995 |
| WO | 96/07637 | 3/1996 |
| WO | 96/24577 | 8/1996 |
| WO | 96/32375 | 10/1996 |
| WO | 98/15526 | 4/1998 |
| WO | 98/17636 | 4/1998 |
| WO | 99/02494 | 1/1999 |
| WO | 99/55674 | 11/1999 |
| WO | 02/50071 | 6/2002 |
| WO | 02/080928 | 10/2002 |
| WO | 02/100352 | 12/2002 |
| WO | 2004/026868 | 4/2004 |
| WO | 2004/094418 | 11/2004 |
| WO | 2005/021539 | 3/2005 |
| WO | 2005/092882 | 10/2005 |
| WO | 2006/050037 | 5/2006 |
| WO | 2006/106425 | 10/2006 |
| WO | 2006/133393 | 12/2006 |
| WO | 2007/018496 | 2/2007 |

(Continued)

OTHER PUBLICATIONS

Asano Toshio et al. "Complex Pain Mechanism—Neuropathic Pain Nociceptive Pain Disease Specific Fibromyalgia", *J. Clinical and Exp. Med.* 211(5):436-436 2004.
Kasahara Mari "Fibromyalgia Syndrome (FMS), Traumatic Stress", *Lecture Series Glossary 7* 6(1):H5-116 (2008).
Nakamura Hiroshi "Pathology and Treatment of Fibromyalgia", *Inflammation and Immune* 12(6):667-673 (2004).
Office Action corresponding to Japanese Application No. 2012-537802 issued Oct. 8, 2014.
PCT/KR2010/007603 International Search Report and Written Opinion dated Jul. 29, 2011 (9 pages).
Al-Muhammed et al., "In-vivo studies on dexamethasone sodium phosphate liposomes," J. Microencapsulation, 1996, vol. 13, No. 3, pp. 293-306.
Arnold et al., "Comorbidity of Fibromyalgia and Psychiatric Disorders," J Clin Psychiatry, Aug. 2006, vol. 67, No. 8, pp. 1219-1225.
Bennett, "Clinical Manifestations and Diagnosis of Fibromyalgia," Rhuem Dis Clin N Am, 2009, vol. 35, pp. 215-232.
Bennett et al., "A peripheral mononeuropathy in rat that produces disorders of pain sensation like those seen in man," Pain, 1988, vol. 33, pp. 87-107.

(Continued)

*Primary Examiner* — Jeffrey S Lundgren
*Assistant Examiner* — William Lee
(74) *Attorney, Agent, or Firm* — Myers Bigel, P.A.

(57) ABSTRACT

The invention is directed to a method of treating fibromyalgia syndrome in a subject, comprising administering a therapeutically effective amount of a carbamoyl compound, or pharmaceutically acceptable salt thereof.

11 Claims, No Drawings

(56) References Cited

FOREIGN PATENT DOCUMENTS

| WO | 2008/048801 | 4/2008 |
|----|-------------|--------|
| WO | WO 2008/067060 A2 | 6/2008 |
| WO | 2011/005473 | 1/2011 |

OTHER PUBLICATIONS

Chonn et al., "Recent advances in liposomal drug-delivery systems," Current Opinion in Biotechnology, 1995, vol. 6, pp. 698-708.
Choy et al., "Safety and tolerability of duloxetine in the treatment of patients with fibromyalgia: pooled analysis of data from five clinical trials," Clin Rheumatol, 2009, vol. 28, pp. 1035-1044.
Eyles et al., "Oral Delivery and Fate of Poly(lactic acid) Microsphere-encapsulated Interferon in Rats," J. Pharm. Pharmacol., 1997, vol. 49, pp. 669-674.
Gao et al., "Controlled Release of a Contraceptive Steroid from Biodegradable and Injectable Gel Formations; In Vitro Evaluation," Pharmaceutical Research, 1995, vol. 12, No. 6, pp. 857-863.
Gendreau et al., " Milnacipran is safe and well tolerated in the treatment of fibromyalgia syndrome," Abstract Only, 2008.
Hargreaves et al., "A new and sensitive method for measuring thermal nociception in cutaneous hyperalgesia," Pain, 1988, vol. 32, pp. 77-88.
Harris et al., "Newer treatments for fibromyalgia syndrome," Therapeutics and Clinical Risk Management, 2008, vol. 4, No. 6, pp. 1331-1342.
Kim et al., "Pregabalin for fibromyalgia: Some relief but no cure," Cleveland Clinic Journal of Medicine, Apr. 2009, vol. 76, No. 4, pp. 255-261.
Mease, "Fibromyalgia Syndrome: Review of Clinical Presentation, Pathogenesis, Outcome Measures, and Treatment," The Journal of Rheumatology, 2005, vol. 32, Suppl. 75, pp. 6-21.
Minto et al., "Pharmacokinetics and Pharmacodynamics of Nandrolone Esters in Oil Vehicle: Effects of Ester, Injection Site and Injection Volume," The Journal of Pharmacology and Experimental Therapeutics, 1997, vol. 281, No. 1, pp. 93-102.
Ostro et al., "Use of liposomes as injectable-drug delivery systems," American Journal of Hospital Pharmacy, Aug. 1989, vol. 46, pp. 1576-1587.
Rohatagi et al., "Pharmacokinetic and Pharmacodynamic Evaluation of Triamcinolone Acetonide After Intravenous, Oral, and Inhaled Administration," J Clin Pharmacol, 1995, vol. 35, pp. 1187-1193.
Tjwa, "Budesonide inhaled via Turbuhaler: a more effective treatment for asthma than beclomethasone dipropionate via Rotahaler," Annals of Allergy, Asthma, & Immunology, Aug. 1995, vol. 75, pp. 107-111.
Verdu et al., "Antidepressants for the Treatment of Chronic Pain," Drugs, 2008, vol. 68, No. 18, pp. 2611-2632.
Rao, "Recent developments of collagen-based materials for medical applications and drug delivery systems," J. Biomater. Sci. Polymer Edn, 1995, vol. 7, No. 7, pp. 623-645.
Allen et al., "MRI Measurement of Brain Iron in Patients with Restless Legs Syndrome", Neurology, vol. 56, pp. 263-265, Jan. 2001.
Azorin et al., "An Update on the Treatment of Bipolar Depression", Expert Opin. Pharmacother., vol. 10, No. 2, pp. 161-172, 2009.
Banno et al., Sleep Medicine (2000) pp. 221-229.
Bayard et al., "Restless Legs Syndrome", American Family Physician, vol. 78, No. 2, pp. 235-240, Jul. 15, 2008.
Cami et al., The New England Journal of Medicine (2003) Massachusetts Medical Society, vol. 349, pp. 975-986.
Chengappa et al., "Barriers to the Effective Management of Bipolar Disorder: A Survey of Psychiatrists Based in the UK and USA", Bipolar Disorders, vol. 7, suppl.1, pp. 38-42, 2005.
Cousins et al., "The Role of Dopamine in Bipolar Disorder", Bipolar Disorders, vol. 11, pp. 787-806, 2009.
Cuellar et al., "Distinctions Between Bipolar and Unipolar Depression", Clin. Psychol. Rev., vol. 25, No. 3, pp. 307-339, May 2005.
Daley, "Update on attention-deficit/hyperactivity disorder, Current Opinion in Pediatrics," 16:217-226, 2004.
Damsma et al, "Lack of tolerance to nicotine-induced dopamine release in the nucleus accumbens," European Journal of Pharmacology (1989) pp. 363-368.
Daughton et al., Review of ADHD Pharmacotherapies: Advantages, Disadvantages, and Clinical Pearls, J. Am. Acad. Child Adolesc. Psychiatry, 48:3, 240-248, Mar. 2009.
Di Chiara et al, "Drugs abused by humans preferentially increase synaptic dopamine concentrations in the mesolimbic system of freely moving rats," Proc. National Accademy of Science, USA, Jul. 1988, vol. 85, pp. 5274-5278.
Ferini-Strambi, "Treatment Options for Restless Legs Syndrome", Expert Opin. Pharmacother., vol. 10, No. 4, pp. 545-554, 2009.
Frye et al., "Unmet Needs in Bipolar Depression", Depression and Anxiety, vol. 19, pp. 1999-208, 2004.
Fulda et al., "Dopamine Agonists for the Treatment of Restless Legs Syndrome", Expert Opin. Pharmacother., vol. 6, No. 15, pp. 2655-2666, 2005.
Garcia-Borreguero et al., "Circadian Variation in Neuroendocrine Response to L-dopa in Patients with Restless Legs Syndrome", Sleep, vol. 27, No. 4, pp. 669-673, 2004.
Grund et al., Behavioral and Brain Functions 2006, 2:2,1-14, 2006.
Harel et al., "Effectiveness and Safety of Adjunctive Antidepressants in the Treatment of Bipolar Depression: A Review", Isr J Psychiatry Relat Sci, vol. 45, No. 2, pp. 121-128, 2008.
Henningfield, "Nicotine Medications for Smoking Cessation," The New England Journal of Medicine, Nov. 2, 1995, vol. 333, No. 18, pp. 1196-1203.
Hornyak "Depressive Disorders in Restless Legs Syndrome", CNS Drugs, vol. 24, No. 2, pp. 89-98, 2010.
Hurt et al, "A Comparison of Sustained-Release Bupropion and Placebo for Smoking Cessation," The New England Journal of MedicineOct. 23, 1997, vol. 337, No. 17, pp. 1195-1202.
Imperato et al, "Nicotine preferentially stimulates dopamine release in the limbic system of freely moving rats," European Journal of Pharmacology (1986) pp. 337-338.
Kessler et al., "Lifetime Prevalence and Age-of-Onset Distributions of DSM-IV Disorders in the National Comorbidity Survey Replication", Arch Gen Psychiatry, vol. 62, pp. 593-602 & 768, Jun. 2005.
Kessler et al., "Prevalence, Severity and Comorbidity of Twelve-month DSM-IV Disorders in the National Comorbidity Survey Replication (NCS-R)", Arch Gen Psychiatry, vol. 62, No. 6, pp. 617-627, Jun. 2005.
Kim et al., "Bupropion May Improve Restless Legs Syndrome", Clin Neuropharmacol, vol. 28, No. 6, pp. 298-301, Nov.-Dec. 2005.
Miklowitz et al., "The Psychopathology and Treatment of Bipolar Disorder", Annu. Rev. Clin. Psychol., vol. 2, 2006.
Miller et al., "Assessment Tools for Adult Bipolar Disorder", Clin Psychol. (New York), vol. 16, No. 2, pp. 188-201, Jun. 1, 2009.
Murphy et al., J Clin Psychiatry 2004; 65:12-17, 2004.
Nisell et al, "Infusion of Nicotine in the Ventral Tegmental Area or the Nucleus Accumbens of the Rat Differentially Affects Accumbal Dopamine Release," Pharmacology & Toxicology, (1994) pp. 348-352.
Nisell et al, "Nicotine Dependence, Midbrain Dopamine Systems and Psychiatric Disorders," Pharmacology & Toxicology (1995) pp. 157-162.
Nisell et al, "Systemic Nicotine-Induced Dopamine Release in the Rat Nucleus Accumbens is Regulated by Nicotinic Receptors in the Ventral Tegmental Area," Synapse (1994) pp. 36-44.
Nunes et al., Journal of the American Medical Association (2004) American Medical Association, vol. 291, pp. 1887-1896.
Ondo, "Restless Legs Syndrome", Neurol Clin, vol. 27, pp. 779-799, 2009.
PCT/KR2009/005863 International Search Report and Written Opinion dated May 28, 2010 (9 pages).
PCT/KR2010/007698 International Search Report and Written Opinion dated Jul. 22, 2011 (8 pages).
Pontieri et al, "Effects of nicotine on the nucleus accumbens and similarity to those of addictive drugs," Letters of Nature, Jul. 18, 1996, vol. 382, pp. 255-257.

(56) References Cited

OTHER PUBLICATIONS

Rader et al., American Family Physician, vol. 79, No. 8, 657-665, 2009.
Rapoport, Stanley, I., et al., "Bipolar Disorder and Mechanisms of Action of Mood Stabilizers", Brain Research Reviews, vol. 61, pp. 185-209, 2009.
Spencer et al., vol. 79, No. 8, 3-9, 2002.
Stiasny-Kolster et al., "Static Mechanical Hyperalgesia Without Dynamic Tactile Allodynia in Patients with Restless Legs Syndrome", Brain, vol. 127, No. 4, pp. 773-782, 2004.
Vieta et al., "Evolving Trends in the Long-Term Treatment of Bipolar Disorder", The World Journal of Biological Psychiatry, vol. 8, No. 1, pp. 4-11, 2007.
Xu et al., Bioorganic and Medicinal Chemistry (2006) Elsevier, vol. 14, pp. 3285-3299.
PCT/KR2011/004677 International Search Report dated Feb. 24, 2012 (4 pages).
PCT/KR2011/004677 International Preliminary Report on Patentability dated Jan. 17, 2013 (7 pages).
European Search Report for Application No. 10828500.8 dated Mar. 12, 2013 (4 pages).
Beers, M. et al., "The Merck Manual of Diagnosis and Therapy" Merck Research Laboratories, Mar. 5, 1999, seventeenth edition, pp. 2254-2259.
European Search Report for Application No. 10828479.5 dated Mar. 27, 2013 (11 pages).
Garcia-Borreguero et al., "Treatment of restless legs syndrome with gabapentin: A double-blind, cross-over study," Neurology, 59, Nov. 2002, p. 1573-1579.
United States Patent Office Action for U.S. Appl. No. 12/827,529 dated Apr. 22, 2013 (10 pages).
Amsterdam Jay D. et al., "A single-site, double-blind, placebo-controlled, dose-ranging study of YKP10A: A putative, new antidepressant", Progress in Neuro-Psychopharmacology & Biological Psychiatry, Dec. 1, 2002, pp. 1333-1338.
Gordon, R. et al., "Pharmacological profile of YKP10A: a novel antidepressant", Abstracts of the annual meeting of the Society of Neuroscience, Jan. 1, 1998.
Hassan et al., "How to Keep the Brain awake? The Complex Molecular Pharmacogenetics of Wake Promotion," Neuropsychopharmacology 34:1625-1640 (2009).
Office Action corresponding to Russian Application No. 2012123154/15(035221) issued Aug. 13, 2014.

* cited by examiner

METHODS FOR TREATING FIBROMYALGIA SYNDROME

STATEMENT OF PRIORITY

This application is a continuation of U.S. application Ser. No. 13/508,145, filed Jun. 13, 2012, currently pending, which is a 35 U.S.C. §371 national phase application of PCT Application No. PCT/KR2010/007603, filed Nov. 1, 2010, which claims the benefit of U.S. Provisional Application No. 61/258,672, filed Nov. 6, 2009. The entire content of each of these applications is incorporated herein by reference.

TECHNICAL FIELD

The present invention relates a method of treating fibromyalgia syndrome. More specifically, the present invention is directed to a method of using a carbamate compound alone or in combination with other medications, for the treatment of fibromyalgia syndrome.

BACKGROUND ART

Fibromyalgia syndrome is a chronic disease involving widespread pain, stiffness and tenderness in musculoskeletal-related tissues including muscles, tendons and ligaments (Bennett, 2009). Patients with fibromyalgia show sleep disturbances, fatigue, anxiety and/or fibrofog. Fibrofog encompasses the inability to concentrate, memory loss and depression. Fibromyalgia occurs in approximately 2% of the United States general population with a higher incidence in women (3.4%) compared to men (0.5%) (Mease, 2005; Arnold et al., 2006).

The core symptom of fibromyalgia is the widespread pain described as arising from muscle and joints (Bennett, 2009). Many patients with fibromyalgia have tender skin. The pain typically increases and decreases in intensity with flares accompanying unusual exertion, prolonged inactivity, soft tissue injuries, surgery, poor sleep, cold exposure, long car trips and stress. Pain is predominately axial in location but can also occur in hands and feet.

Fatigue is a common symptom for fibromyalgia patients. Fatigue while used interchangeably with sleepiness has been described as a weariness of mind and body that impairs productivity and enjoyment of life (Bennett, 2009). Treatment with antidepressants results in only a modest improvement of fatigue suggesting that there is more to the fatigue symptom than depression. Increased restorative sleep is not sufficient alone to reduce fatigue.

Sleep patterns are commonly disturbed in patients with fibromyalgia (Bennett, 2009). There are issues with sleep initiation and sleep maintenance but patients feel tired when they awaken thus excessive daytime sleepiness results in greater incompatibility with daily functioning than initiation and maintenance of sleep.

Tenderness is typically reported by patients with fibromyalgia where there is sensitivity to touch and pain is experienced even after minor contact (Bennett, 2009). The duration of widespread pain must be of at least three months and tenderness must occur at 11 or more of 18 specific tender spots in order to be classified as fibromyalgia (Mease, 2005; Arnold et al., 2006). In addition, difficulties with memory, concentration and dual tasking are reported issues by fibromyalgia patients.

Fibromyalgia has been shown to be comorbid with bipolar disorder, major depressive disorder, any anxiety disorder, any eating disorder and any substance abuse disorder (Arnold et al, 2006). These diseases may share underlying pathophysiological links and treatment should be chosen with comorbid presenting features in mind.

While the etiology of fibromyalgia is unknown, there is evidence to suggest some abnormalities in central monoaminergic neurotransmission including serotonin and norepinephrine systems (Verdu et al., 2008). Tricyclic antidepressants (TCAs) and SNRIs have been explored as treatment for fibromyalgia. TCAs including amitriptyline, and cyclobezaprine showed modest efficacy with improvements in self-ratings of pain, stiffness, fatigue, sleep and tenderness. Limited and inconsistent results were obtained for SRIs included fluoxetine and citalopram. Positive results were obtained for SNRIs including duloxetine and milnacipran with better improvement in tenderness compared to TCAs and these compounds were specifically approved for fibromyalgia treatment by the FDA in 2007 and 2009, respectively.

Antidepressants used to treat fibromyalgia show adverse reactions in a significant percent of patients (Verdu et al., 2008). It has been shown that progressive introduction of antidepressants increased tolerability. TCAs show mouth dryness, constipation and urinary and bowel emptying difficulties; effects associated with anticholinergic properties. Sedation, drowsiness and orthostatic hypotension are also common. Common side effects of SRI are associated with the actions of serotonin and include nausea, gastric discomfort, vomiting, anorexia, diarrhea and skin hyperhydrosis. In addition, there is a risk of physical dependence and withdrawal with abrupt cessation of treatment with antidepressants. Furthermore, antidepressants typically interfere with sexual function and desire. Duloxetine was assessed for tolerability across five clinical trials of over 6 months in duration and the most common side effects included nausea, headache, dry mouth, insomnia, fatigue, constipation, diarrhea and dizziness (Choy et al., 2009) with about 20% of patients discontinuing due to adverse effects. Although milnacipran was generally well tolerated, approximately twice as patients in the treated groups withdrew from the study due to adverse effects including nausea, constipation, palpitations, and flushing compared to those in the placebo-treated group (Harris & Clauw, 2008).

Antiepileptic drugs including gabapentin and pregabalin have been prescribed to patients with neuropathic pain subtypes and fibromyalgia (Mease, 2005). Pregabalin was the first drug approved for fibromyalgia in 2007 by the FDA. Pregabalin has demonstrated efficacy in several recent fibromyalgia trials with improved pain scores, quality of sleep and fatigue (Kim et al., 2009). Common side effects of pregabalin included dizziness, sleepiness and weight gain. Less common side effects are difficulty concentrating and paying attention, dry mouth and blurred vision. Pregabalin is also a scheduled compound at Schedule V suggesting some potential for abuse and withdrawal symptoms. Thus, while pregabalin showed reduced pain in some patients, there is still room for improvement of both efficacy and side effect profile.

Other compounds that may be useful in treating fibromyalgia include monoamine oxidase inhibitors (i.e., pirlindole), 5-HT3 antagonists (i.e., tropisetron), opioids, tramadol, muscle relaxants, NMDA receptor antagonists and dopamine agonists (i.e., pramipexole) (Mease, 2005). Many of these compounds show either weak efficacy, less broad spectrum efficacy for symptoms or intolerable side-effect profiles included drug dependence.

DISCLOSURE OF INVENTION

Technical Problem

Accordingly, there is a need in the treatment of fibromyalgia syndrome that would improve efficacy in the treatment of pain, sleep, fatigue and other comorbidities including depression and reduce side effect profiles.

Solution to Problem

The present invention is directed to a method of treating fibromyalgia syndrome comprising the administration of a therapeutically effective amount of a compound having structural Formula (1) or a pharmaceutically acceptable salt thereof, to a mammal in need of treatment:

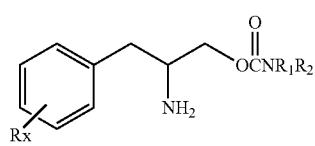
(1)

wherein,

R is selected from the group consisting of hydrogen, lower alkyl of 1 to 8 carbon atoms, halogen selected from F, Cl, Br and I, alkoxy of 1 to 3 carbon atoms, nitro group, hydroxy, trifluoromethyl, and thioalkoxy of 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms;

$R_1$ and $R_2$ can be joined to form a 5 to 7-membered heterocycle substituted with a member selected from the group consisting of hydrogen, alkyl, and aryl groups, wherein the heterocyclic compound comprises 1 to 2 nitrogen atoms and 0 to 1 oxygen atom, and the nitrogen atoms are not directly connected with each other or with the oxygen atom.

In another embodiment, the present invention provides a method of improving symptoms associated with fibromyalgia syndrome in a subject, comprising the step of the administration, to a subject in need of such treatment, of a therapeutically effective amount a compound of the Formula (1) or a pharmaceutically acceptable salt thereof.

In further embodiment, the present invention provides a method of ameliorating or eliminating effects of fibromyalgia syndrome in a subject, comprising the step of the administration, to a subject in need of such treatment, of a therapeutically effective amount a compound of the Formula (1) or a pharmaceutically acceptable salt thereof.

In additional embodiment, the present invention is directed to pharmaceutical composition for treating fibromyalgia syndrome comprising a therapeutically effective amount a compound of the Formula (1) or a pharmaceutically acceptable salt thereof.

In another embodiment, the present invention provides a pharmaceutical composition for improving symptoms associated with fibromyalgia syndrome in a subject, comprising a therapeutically effective amount a compound of the Formula (1) or a pharmaceutically acceptable salt thereof.

In further embodiment, the present invention provides a pharmaceutical composition for ameliorating or eliminating symptoms of fibromyalgia syndrome in a subject, comprising a therapeutically effective amount a compound of the Formula (1) or a pharmaceutically acceptable salt thereof.

The compound having structural Formula (1) is an enantiomer substantially free of other enantiomers or an enantiomeric mixture wherein one enantiomer of the compound having structural Formula (1) predominates. One enantiomer predominates to the extent of about 90% or greater, and preferably about 98% or greater.

The enantiomer is (S) or (L) enantiomer as represented by Structural Formula (1a) or (R) or (D) enantiomer, as represented by Structural Formula (1b):

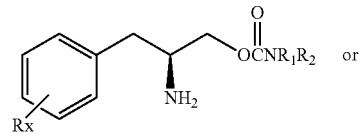
(1a)

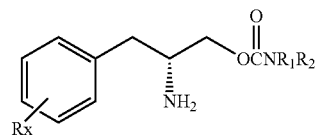
(1b)

Preferably, Rx, $R_1$ and $R_2$ are all selected from hydrogen and x is 1, which are shown in the following formula:

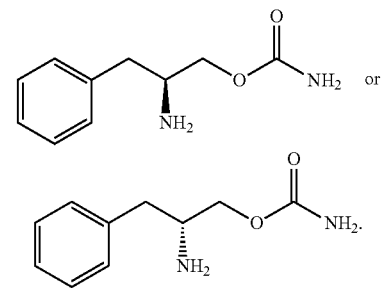

Embodiments of the invention include a method for using the enantiomer of Formula 1 substantially free of other enantiomers that is the enantiomer of Formula 1b or an enantiomeric mixture wherein the enantiomer of Formula 1b predominates. (Note: in the structural formula of Formula 1b below the amino group attached to the beta carbon projects into the plane of the paper. This is the dextrorotary (D) enantiomer that is of absolute configuration (R))

Advantageous Effects of Invention

The present invention is based in part on the discovery that phenylalkylamino carbamates of Formula 1 discussed above have novel and unique pharmacological properties. These compounds have been shown in several animal models to have the ability to treat fibromyalgia syndrome and modification of symptoms associated with fibromyalgia syndrome.

Although the precise mechanism of action is not completely understood, it is known that these compounds do not work by the same mechanisms as most other known treatments for fibromyalgia syndrome. For these reasons, the compounds of Formula 1 are especially suitable for use as sole or adjunctive treatment for fibromyalgia and modification of symptoms associated with fibromyalgia syndrome.

BEST MODE FOR CARRYING OUT THE INVENTION

These and other objects of the invention will be more fully understood from the following description of the invention and the claims appended hereto.

The present invention is directed to a method of treating fibromyalgia syndrome comprising the administration of a therapeutically effective amount of a compound having structural Formula (1) or enantiomers, diastereomers, racemates or mixtures thereof, or hydrates, solvates and pharmaceutically acceptable salts and amides thereof, to a mammal in need of treatment:

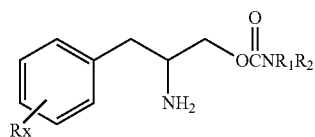

(1)

wherein,

R is selected from the group consisting of hydrogen, lower alkyl of 1 to 8 carbon atoms, halogen selected from F, Cl, Br and I, alkoxy of 1 to 3 carbon atoms, nitro group, hydroxy, trifluoromethyl, and thioalkoxy of 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, cycloalkyl of 3 to 7 carbon atoms;

$R_1$ and $R_2$ can be joined to form a 5 to 7-membered heterocycle substituted with a member selected from the group consisting of hydrogen, alkyl, and aryl groups, wherein the heterocyclic compound comprises 1 to 2 nitrogen atoms and 0 to 1 oxygen atom, and the nitrogen atoms are not directly connected with each other or with the oxygen atom.

The present method also includes the use of a compound selected from the group consisting Formula 1a or 1b, or enantiomers, diastereomers, racemates or mixtures thereof, or hydrates, solvates and pharmaceutically acceptable salts and amides thereof:

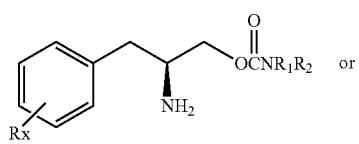

(1a)

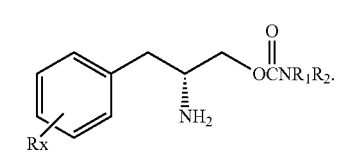

(1b)

wherein Rx, $R_1$ and $R_2$ are the same as defined above.

The present method also preferably includes the use of the D (or dextrorotary) enantiomer (of absolute configuration R) selected from the group consisting of Formula 1 or an enantiomeric mixture thereof. In the structural formula of Formula 1b, the amino group attached to the beta carbon projects into the plane of the paper. This is the dextrorotary (D) enantiomer that is of absolute configuration (R).

Preferably, in the Structural Formula 1, Rx, $R_1$ and $R_2$ are hydrogen and x is 1 as represented by following Structural Formula:

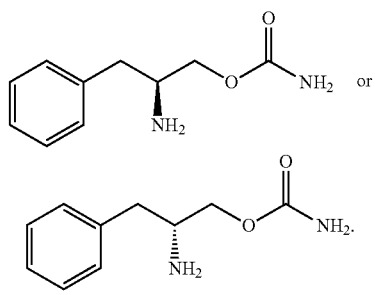

O-carbamoyl-(D)-phenylalaminol is also named (R)-(beta-amino-benzenepropyl) carbamate monohydrochloric acid. For enantiomeric mixtures, wherein O-carbamoyl-(D)-phenylalaminol predominates, preferably, to the extent of about 90% or greater, and more preferably about 98% or greater.

The compounds of Formula 1 can be synthesized by methods known to a skilled person in the art. Some reaction schemes for synthesizing compounds of Formula (1) have been described in published; U.S. Pat. Nos. 5,705,640, 5,756,817, 5,955,499, and 6,140,532. Details of the above reactions schemes as well as representative examples on the preparation of specific compounds have been described in published; U.S. Pat. Nos. 5,705,640, 5,756,817, 5,955,499, 6,140,532, all incorporated herein by reference in their entirety.

The salts of the compounds of Formula (1) can be produced by treating the compound with an acid (HX) in suitable solvent or by means well known to those of skill in the art.

From Structural Formula 1, it is evident that some of the compounds of the invention have at least one and possibly more asymmetric carbon atoms. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W.

McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known from the art.

The present invention is based in part on the discovery that phenylalkylamino carbamates of Formula 1 discussed above have novel and unique pharmacological properties. These compounds have been shown in several animal models to have the ability to treat fibromyalgia syndrome and modification of symptoms associated with fibromyalgia syndrome.

Although the precise mechanism of action is not completely understood, it is known that these compounds do not work by the same mechanisms as most other known treatments for fibromyalgia syndrome. For these reasons, the compounds of Formula 1 are especially suitable for use as sole or adjunctive treatment for fibromyalgia and modification of symptoms associated with fibromyalgia syndrome.

Thus, these compounds can be safely used alone or in combination with other useful medications to provide enhanced efficacy and reduced side effects because smaller doses of each drug that could be used.

In one aspect, this invention relates to methods to treat subjects suffering from fibromyalgia syndrome; the method comprising delivering to the subject a therapeutically effective amount of one or more of the carbamate compounds of the invention or a pharmaceutically acceptable salt thereof and a pharmaceutically acceptable carrier, diluent or excipient.

In another aspect, this invention also provides a method for diminishing, inhibiting or eliminating the symptoms of fibromyalgia syndrome including depression, sleep disturbances and fatigue in a subject suffering from fibromyalgia syndrome which comprises administering to the subject an effective amount of carbamate compounds of the invention to diminish, inhibit or eliminate said symptoms.

Definitions

For convenience, certain terms employed in the specification, examples, and appended claims are collected here.

It is to be understood that this invention is not limited to the particular methodology, protocols, animal species or genera, and reagents described, as such may vary. It is also to be understood that the terminology used herein is for the purpose of describing particular embodiments only, and is not intended to limit the scope of the present invention that will be limited only by the appended claims.

As used herein the term "subject" refers to an animal, preferably a mammal, and most preferably a human both male and female, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the signs or symptoms of the disease or disorder being treated.

The term "prophylactically effective amount" is intended to mean that amount of a pharmaceutical drug that will prevent or reduce the risk of occurrence of the biological or medical event that is sought to be prevented of a tissue, a system, animal or human that is being sought by a researcher, veterinarian, medical doctor or other clinician.

The term "pharmaceutically acceptable salts" shall mean non-toxic salts of the compounds employed in this invention which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, valerate.

Therefore, the term "a patient in need of treatment" as used herein will refer to any subject or patient who currently has or may develop any of the above syndromes or disorders, including any mood disorder which can be treated by antidepressant medication, or any other disorder in which the patient s present clinical condition or prognosis could benefit from the administration of one or more compounds of Formula (1) alone or in combination with another therapeutic intervention including but not limited to another medication.

The term "treating" or "treatment" as used herein, refers to any indicia of success in the prevention or amelioration of an injury, pathology or condition of fibromyalgia syndrome and modification of symptoms of fibromyalgia syndrome, including any objective or subjective parameter such as abatement; remission; diminishing of symptoms or making the injury, pathology, or condition more tolerable to the patient; slowing in the rate of degeneration or decline or worsening of the illness; making the final point of worsening less debilitating; or improving a subject's physical or mental well-being. The treatment or amelioration of symptoms can be based on objective or subjective parameters; including the results of a physical examination, neurological examination, and/or psychiatric evaluations. Accordingly, the term "treating" or "treatment" includes the administration of the compounds or agents of the present invention for treatment of any form of fibromyalgia syndrome in both males and females. In some instances, treatment with the compounds of the present invention will done in combination with other compounds to prevent, inhibit, or arrest the progression of the fibromyalgia syndrome.

The term "therapeutic effect" as used herein, refers to the effective improvement in or reduction of symptoms of fibromyalgia syndrome. The term "a therapeutically effective amount" as used herein means a sufficient amount of one or more of the compounds of the invention to produce a therapeutic effect, as defined above, in a subject or patient in need of such fibromyalgia treatment.

The terms "subject" or "patient" are used herein interchangeably and as used herein mean any mammal including but not limited to human beings including a human patient or subject to which the compositions of the invention can be administered. The term mammals include human patients, both male and female and non-human primates, as well as experimental animals such as rabbits, rats, and mice, and other animals.

Methods are known in the art for determining therapeutically and prophylactically effective doses for the instant pharmaceutical composition. For example the compound can be employed at a daily dose in the range of about 0.1 mg to 400 mg usually on a regimen of 1 to 2 times per day, for an average adult human. The effective amount, however, may be varied depending upon the particular compound used, the mode of administration, the strength of the preparation, the mode of administration, and the advancement of the disease condition. In addition, factors associated with the particular patient being treated; including patient age, weight, diet and time of administration, will result in the need to adjust dosages.

The compound may be administered to a subject by any conventional route of administration, including, but not limited to, intravenous, oral, subcutaneous, intramuscular, intradermal and parenteral. Depending on the route of administration, compounds of Formula (1) can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

To prepare the pharmaceutical compositions of this invention, one or more compounds of formula (1) or salt thereof as the active ingredient is intimately admixed with a pharmaceutical carrier according to conventional pharmaceutical compounding techniques. Carriers are necessary and inert pharmaceutical excipients, including, but not limited to, binders, suspending agents, lubricants, flavorings, sweeteners, preservatives, dyes, and coatings. In preparing compositions in oral dosage form, any of the usual pharmaceutical carriers may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. The tablets or pills can be coated or otherwise compounded to provide a dosage form affording the advantage of prolonged action. For example, the tablet or pills can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxypropyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Preferably these compositions are in unit dosage forms such as tablets, pills, capsules, powders, granules, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation.

Alternatively, the composition may be presented in a form suitable for once-weekly or once-monthly administration; for example, an insoluble salt of the active compound, such as the decanoate salt, may be adapted to provide a depot preparation for intramuscular injection.

The pharmaceutical compositions herein will contain, per dosage unit, e.g., tablet, capsule, powder, injection, teaspoonful, suppository and the like, an amount of the active ingredient necessary to deliver an effective dose as described above. For example, the pharmaceutical compositions herein can contain, per unit dosage unit, from about 25 to about 400 mg of the active ingredient. Preferably, the range is from about 50 to about 200 mg of the active ingredient.

In some embodiments of the present invention carbamate compounds suitable for use in the practice of this invention will be administered either singly or concomitantly with at least one or more other compounds or therapeutic agents. In these embodiments, the present invention provides methods to treat fibromyalgia syndrome and modification of symptoms associated with fibromyalgia syndrome in a patient. The method includes the step of; administering to a patient in need of treatment, an effective amount of one of the carbamate compounds disclosed herein in combination with an effective amount of one or more other compounds or therapeutic agents.

It is understood that substituents and substitution patterns on the compounds of the present invention can be selected by one of ordinary skill in the art to provide compounds that are chemically stable and that can be readily synthesized by techniques known in the art as well as the methods provided herein.

The present invention includes the use of isolated enantiomers of Formula 1. In one preferred embodiment, a pharmaceutical composition comprising the isolated S-enantiomer of Formula 1 is used to provide fibromyalgia syndrome treatment in a subject. In another preferred embodiment, a pharmaceutical composition comprising the isolated R-enantiomer of Formula 1 is used to provide fibromyalgia syndrome treatment a subject The present invention also includes the use of mixtures of enantiomers of Formula 1. In one aspect of the present invention, one enantiomer will predominate. An enantiomer that predominates in the mixture is one that is present in the mixture in an amount greater than any of the other enantiomers present in the mixture, e.g., in an amount greater than 50%. In one aspect, one enantiomer will predominate to the extent of 90% or to the extent of 91%, 92%, 93%, 94%, 95%, 96%, 97% or 98% or greater. In one preferred embodiment, the enantiomer that predominates in a composition comprising a compound of Formula 1 is the S-enantiomer of Formula 1.

The present invention provides methods of using enantiomers and enantiomeric mixtures of compounds represented by Formula 1. A carbamate enantiomer of Formula 1 contains a chiral center on the second aliphatic carbon adjacent to the phenyl ring. An enantiomer that is isolated is one that is substantially free of the corresponding enantiomer. Thus, an isolated enantiomer refers to a compound that is separated via separation techniques or prepared free of the corresponding enantiomer. The term "substantially free", as used herein, means that the compound is made up of a significantly greater proportion of one enantiomer. In preferred embodiments, the compound includes at least about 90% by weight of a preferred enantiomer. In other embodiments of the invention, the compound includes at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein.

Carbamate Compounds as Pharmaceuticals:

The present invention provides racemic mixtures, enantiomeric mixtures and isolated enantiomers of Formula 1 as pharmaceuticals. The carbamate compounds are formulated as pharmaceuticals to provide anti-fibromyalgia action in a subject.

In general, the carbamate compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection.) Administration of the compounds directly to the nervous system can include, for example, administration to intracerebral, intraventricular, intacerebroventricular, intrathecal, intracisternal, intraspinal or peri-spinal routes of administration by delivery via intracranial or intravertebral needles or catheters with or without pump devices.

Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: *Remington's Pharmaceutical Sciences,* 17th ed., Mack Publishing Company, Easton Pa., 1985, the disclosure of which is incorporated herein by reference in its entirety and for all purposes. Suitable liquid carriers, especially for injectable solutions, include water, aqueous saline solution, aqueous dextrose solution, and glycols.

The carbamate compounds can be provided as aqueous suspensions. Aqueous suspensions of the invention can contain a carbamate compound in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate).

The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions for use in the present methods can be formulated by suspending a carbamate compound in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these.

Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations of the present invention suitable for parenteral administration, such as, for example, by intraarticular (in the joints), intravenous, intramuscular, intradermal, intraperitoneal, and subcutaneous routes, can include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter.

Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well-known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The concentration of a carbamate compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally acceptable diluents or solvent, such as a solution of 1,3-butanediol. The formulations of commends can be presented in unit-dose or multi-dose sealed containers, such as ampoules and vials. Injection solutions and suspensions can be prepared from sterile powders, granules, and tablets of the kind previously described.

A carbamate compound suitable for use in the practice of this invention can be and is preferably administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 50% w of the carbamate compound, preferably 0.00001% w to 25% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient.

Formulations suitable for oral administration can consist of (a) liquid solution, such as an effective amount of the pharmaceutical formulation suspended in a diluents, such as water, saline or polyethyleneglycol (PEG) 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethyl-cellulose; and gums including arabic and tragacanth; as well as proteins such as gelatin and collagen.

If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient that is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug (e.g., mifepristone)-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention.

In another embodiment, the compounds of the present invention can be delivered by the use of liposomes which fuse with the cellular membrane or are endocytosed, i.e., by employing ligands attached to the liposome that bind to surface membrane protein receptors of the cell resulting in endocytosis. By using liposomes, particularly where the liposome surface carries ligands specific for target cells, or are otherwise preferentially directed to a specific organ, one can focus the delivery of the carbamate compound into target cells in vivo. (See, e.g., Al-Muhammed, J. Microencapsul. 13:293-306, 1996; Chonn, Cliff. Opin. Biotechnol. 6:698-708, 1995; Ostro, Am. J. Hosp. Pharm. 46:1576-1587, 1989).

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation can be a lyophilized powder which can contain, for example, any or all of the following: 1 mM-50 mM histidine, 0.1%-2% sucrose, 2%-7% mannitol, at a pH range of 4.5 to 5.5, that is combined with buffer prior to use.

Pharmaceutically acceptable salts refer to salts that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N methylglucamine, and the like. Pharmaceutically acceptable salts can also include acid addition salts formed from the reaction of amine moieties in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

Compounds named in this invention can be present in unsalified form, or in salified form, and the naming of such compounds is intended to include both the original (unsalified) compound and its pharmaceutically acceptable salts. The present invention includes pharmaceutically acceptable salt forms of Formula (1). More than one crystal form of an enantiomer of Formula 1 can exist and as such are also included in the present invention.

A pharmaceutical composition of the invention can optionally contain, in addition to a carbamate compound, at least one other therapeutic agent useful in the treatment of fibromyalgia syndrome. For example, the carbamate compounds of Formula 1 can be combined physically with other fibromyalgia treatments in fixed dose combinations to simplify their administration.

Methods of formulating pharmaceutical compositions have been described in numerous publications such as *Pharmaceutical Dosage Forms: Tablets*. Second Edition. Revised and Expanded. Volumes 1-3, edited by Lieberman et al; *Pharmaceutical Dosage Forms*: Parenteral Medications, Volumes 1-2, edited by Avis et al; and *Pharmaceutical Dosage Forms: Disperse Systems*. Volumes 1-2, edited by Lieberman et al; published by Marcel Dekker, Inc, the disclosure of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

Dosage Regimens

The present invention provides methods of providing anti-fibromyalgia action in a mammal using carbamate compounds. The amount of the carbamate compound necessary to reduce or treat fibromyalgia syndrome is defined as a therapeutically or a pharmaceutically effective dose. The dosage schedule and amounts effective for this use, i.e., the dosing or dosage regimen will depend on a variety of factors including the stage of the disease, the patient's physical status, age and the like. In calculating the dosage regimen for a patient, the mode of administration is also taken into account.

A person of ordinary skill in the art will be able without undue experimentation, having regard to that skill and this disclosure, to determine a therapeutically effective amount of a particular substituted carbamate compound for practice of this invention (see, e.g., Lieberman, Pharmaceutical Dosage Forms (Vols. 1-3, 1992); Lloyd, 1999, The art, Science and Technology of Pharmaceutical Compounding; and Pickar, 1999, Dosage Calculations). A therapeutically effective dose is also one in which any toxic or detrimental side effects of the active agent that is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

For treatment purposes, the compositions or compounds disclosed herein can be administered to the subject in a single bolus delivery, via continuous delivery over an extended time period, or in a repeated administration protocol (e.g., by an hourly, daily or weekly, repeated administration protocol). The pharmaceutical formulations of the present invention can be administered, for example, one or more times daily, 3 times per week, or weekly. In one embodiment of the present invention, the pharmaceutical formulations of the present invention are orally administered once or twice daily.

In this context, a therapeutically effective dosage of the carbamate compounds can include repeated doses within a prolonged treatment regimen that will yield clinically significant results to treat fibromyalgia syndrome. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

In an exemplary embodiment of the present invention, unit dosage forms of the compounds are prepared for standard administration regimens. In this way, the composition can be subdivided readily into smaller doses at the physician's direction. For example, unit dosages can be made up in packeted powders, vials or ampoules and preferably in capsule or tablet form.

The active compound present in these unit dosage forms of the composition can be present in an amount of, for example, from about 10 mg to about one gram or more, for single or multiple daily administration, according to the particular need of the patient. By initiating the treatment regimen with a minimal daily dose of about one gram, the blood levels of the carbamate compounds can be used to determine whether a larger or smaller dose is indicated.

Effective administration of the carbamate compounds of this invention can be administered, for example, at an oral or parenteral dose of from about 0.01 mg/kg/dose to about 150 mg/kg/dose. Preferably, administration will be from about 0.1 mg/kg/dose to about 25 mg/kg/dose, more preferably from about 0.2 to about 18 mg/kg/dose. Therefore, the therapeutically effective amount of the active ingredient contained per dosage unit as described herein can be, for example, from about 1 mg/day to about 7000 mg/day for a subject having, for example, an average weight of 70 kg.

The methods of this invention also provide for kits for use in providing treatment of fibromyalgia syndrome. After a pharmaceutical composition comprising one or more carbamate compounds of this invention, with the possible addition of one or more other compounds of therapeutic benefit, has been formulated in a suitable carrier, it can be placed in an appropriate container and labeled for providing fibromyalgia syndrome treatment. Additionally, another pharmaceutical comprising at least one other therapeutic agent useful in the fibromyalgia syndrome treatment can be placed in the container as well and labeled for treatment of the indicated disease. Such labeling can include, for example, instructions concerning the amount, frequency and method of administration of each pharmaceutical.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation. The following examples are provided to illustrate specific aspects of the invention and are not meant to be limitations.

A better understanding of the present invention may be obtained in light of the following examples that are set forth to illustrate, but are not to be construed to limit, the present invention.

Mode for the Invention

EXAMPLE 1

The test compound (O-carbamoyl-(D)-phenylalaminol) administered at 30 mg/kg intraperitoneally (IP) significantly increased paw withdrawal latency to a thermal stimulus in rats with sciatic nerve ligation. These data suggest that the test compound shows anti-thermal hyperalgesic properties.

(Methods)

Young adult male Sprague-Dawley rats (CD(SD)IGS, 150-200 g) were initially anesthetized with isoflurane in $O_2$ by a mask and the surgical procedure was performed according to the method described by Bennett and Xie (1988). Briefly, the right sciatic nerves were loosely tied using ligatures. All experiments were conducted in accordance with the guidelines of the International Association for the Study of Pain. The behavioral tests were conducted at least 14 days postoperatively.

The test compound was dissolved in saline and administered intraperitoneally at 30 mg/kg to animals in a volume of 3 mL/kg body weight.

To test for thermal hyperalgesia, the thermal response was determined by the hindpaw withdrawal latency, using a plantar tester (UGO BASILE, Italy), and a modified method of Hargreaves et al. (1988). Rats were allowed to acclimate within plastic enclosures on a clear glass plate maintained at room temperature. A radiant heat source (intensity 90) was controlled with a timer and focused onto the plantar surface of the rat right hind paw encompassing the glabrous skin. Paw withdrawal stopped both heat source and timer. A maximal cut-off 30 sec was used to prevent tissue damage. Rats were assessed for thermal hyperalgesia predose (0 hr) and at 1, 4 and 8 hours after 30 mg/kg test compound administration.

Data are expressed as mean±standard error of mean (SEM). The values of behavioral signs of neuropathic pain at various postoperative time points were compared with those of the preoperative control period by a repeated-measure One-way Analysis of Variance (followed by Dunnett's post-hoc test). P-values less than 0.05 were considered to be significant.

(Results)

The anti-heat hyperalgesic effects of test compound in the nerve-injured rats are displayed in Table 1 below. The test compound, administered intraperitoneally to rats, significantly increased the paw withdrawal latency to noxious thermal stimuli in comparison with the pre-injection (0 hr) withdrawal latency at 30 mg/kg, IP.

TABLE 1

Anti-thermal hyperalgesic effects (mean paw withdrawal latency in seconds) of the test compound

| Drug Dose | Time Post-Injection | | | |
|---|---|---|---|---|
| (mg/kg, IP) | 0 hr | 1 hr | 4 hr | 8 hr |
| Test Compound (30, n = 6) | 5.17 0.27 | 6.33 ± 0.14**(22.3% @) | 6.06 ± 0.21*(17.2%) | 5.63 ± 0.16(8.8%) |

Data are expressed as mean paw withdrawal latency (sec) ± SEM
*P < 0.05,
**P < 0.01 vs. Paw withdrawal latency (sec) at 0 hr
@ % of Antagonism: [((Paw withdrawal latency (sec) at each time point/Paw withdrawal latency (sec) at 0 hr) − 1)] × 100

EXAMPLE 2

The effects of the test compound (50-150 mg/kg, PO) on various sleep parameters were evaluated in 8 hypocretin cell ablated narcoleptic mice (prepororexin/ataxin-3 transgenic) and their littermate wild-type mice, and the effects were compared with those of modafinil, a reference wake-promoting compound. The test compound showed significantly increased bouts of wakefulness in both wild-type and narcoleptic mice and was able to normalize sleep patterns of narcoleptic mice.

(Methods)

The polygraph signal (EEG and EMG) was captured with SleepSign (Kissel Comtech), and the sleep stage was visually scored with 10 sec epoch for wakefulness, non-REM sleep and REM sleep. Scoring criteria are: Wakefulness is characterized by desynchronized low-amplitude, mixed frequency (>4 Hz) EEG and high EMG activity. Rhythmic alpha (8-9 Hz) wave (with high EMG activities) may also appear. Non-REM is characterized by synchronized, high-amplitude, low-frequency (0.25-4 Hz) with reduced EMG activity (compared to wakefulness). EEG activity in REM sleep is similar to that in wakefulness, with desynchronized, mixed frequency low amplitude waves. Rhythmic alpha (8-9 Hz) wave with reduced EMG activities may also appear. EEG activity during REM sleep is reduced even further and in many cases, completely absent. Some muscle twitching may be apparent in the EMG trace during REM sleep.

Three drug doses of the test compound (50, 100 and 150 mg/kg PO) plus vehicle, was orally administered at ZT 2 (2 hours after light on) or ZT 14 (2 hours after light off), and the effects on sleep was monitored for 6 hours after the drug administration (the sleep data was collected for 30 hours after the drug injection, and are available for further analysis). The doses for modafinil were 50 and 200 mg/kg PO (plus vehicle), and modafinil was also administered at ZT 2 and ZT14.

If the polygraph signals of some mice were not sufficient to score the sleep stage with accuracy (especially bad EMG), data from these animals were excluded, and the minimum of 5 animals (except for the highest dose of the test compound in wild-type mice in dark period, n=4) were included for the data analysis and number of animals were indicated in the figures.

Effects of test compound and modafinil on the amount of wake, non-REM sleep, REM sleep (cumulative seconds), number of episodes for each sleep stage during 6 hours, mean wake/sleep-bout lengths (seconds) were analyzed in each animal and the mean of each parameter was calculated in each genotype. The effects of compounds on wake and sleep amounts are useful to evaluate the wake promoting potency, and the number of episodes for each sleep stage and the mean wake/sleep bout length are parameters for evaluating the sleep fragmentation. Amphetamine and modafinil, two main wake-promoting compounds currently used for the treatment of EDS associated with various etiologies (narcolepsy, idiopathic hypersomnia and secondary EDS), are known to increase wake time and prolong wake bout length in normal and EDS conditions.

With these data analyses, the wake-promoting and therapeutic effects of test compound in narcolepsy were evaluated, and the effects were compared with those of modafinil. A comparison of the effects between hypocretin deficient and wild-type mice is very useful in determining if the wake-promotion of the test compound is dependent on the availability of hypocretins, and if there is a possible change in the sensitivity of the receptive mechanisms of test compound in narcoleptic mice due to the hypocretin ligand deficiency.

(Results)

Effects on Sleep During the Resting Period:

Very potent wake-promoting effects of test compound in both wild-type and hypocretin-deficient narcoleptic mice were observed. The effects were dose-dependent, and administrations of 50, 100, 150 mg/kg PO of test compound induced continuous wakefulness in most wild-type and narcoleptic mice for up to 3, 4 and 5 hours, respectively. During this period, Non-REM and REM sleep were completely suppressed. There were no abnormal EEG patterns after test compound administration, and sleep that occurred after the prolonged wakefulness was normal by polygraphic assessments.

In contrast, the wake promoting effects of modafinil were modest, and the wake promoting effect of 200 mg/kg of modafinil roughly corresponds to 50 mg/kg of test compound. However, modafinil did not strongly reduce REM sleep after the administration of 50 mg/kg of test compound. Furthermore, test compound potently reduced REM sleep, and this contrasts to the effects of modafinil.

Effects on Sleep During the Active Period:

The same experiment was repeated by administrating compounds in the active period. During the active period, narcoleptic mice spend more in sleep than wild-type mice. Wild-type animals typically stayed awake for almost three hours after vehicle administration. Similar to the effects observed during the light period, test compound dose-dependently increased wakefulness in both wild and narcoleptic mice. Wake-promoting effects in wild-type mice were however, subtle during the dark period due to the high amount of wakefulness at the baseline, and only small effects were observed. In contrast, much pronounced wake-promoting effects were observed in narcoleptic mice, and wake amounts in these mice after 100 and 150 mg/kg test compound administration were brought up to the levels of wild-type mice, suggesting that this compound normalizes the sleep/wake amount of narcoleptic mice. Similarly non-REM and REM sleep were reduced in narcoleptic mice by test compound and the amounts of non-REM and REM sleep were also brought down to the levels of wild-type mice. Similar, but much weaker effects were also seen after modafinil administration in these mice. Although modafinil dose-dependently increase wakefulness in narcoleptic mice, the high dose of modafinil (200 mg/kg) did not bring the wake amount to that of the wild-type baseline levels.

EXAMPLE 3

The test compound was tested for the effects on the forced swimming test, an animal model of depression, in both mice and rats. After single doses of the test compound the mean duration of immobility was reduced with an ED50 of 16.6 mg/kg PO in mice and 18.5 mg/kg PO in rats. The test compound was even more potent after multiple dosing in mice with an ED50 of 5.5 mg/kg PO. These data suggest that the test compound shows antidepressant properties.

(Methods)

Male CD-1 mice (16-24 g) and male Wistar rats (90-125 g) were utilized in these experiments. The test compound (10, 15 and 30 mg/kg) was dissolved in physiological saline (0.9%) and administered orally PO in a volume of 1 mL/100 g body weight.

Mice and rats were placed in glass cylinders (1000 ml beakers; height 14 cm, diameter 11.5 cm) and (4000 ml beakers; height 24.5 cm, diameter 18.0 cm) respectively, containing water (25 degrees Celsius) up to a height of 9.0 cm for mice and 19.0 for rats. Each mouse or rat was placed in the glass cylinder and allowed to swim for 2 minutes, following which, they were observed for a period of 4 minutes for signs of immobility. Immobility was defined as lack of movement, such as floating in the water with little or no movement of hind legs. Duration of immobility was timed with a stopwatch and recorded. In some experiments, mice or rats were allowed to swim for 6 or 10 minutes, respectively, one day prior to the forced swimming experiment.

In the single dose test, mice or rats were given test compound or 0.9% NaCl and placed in glass cylinders 1 hour or 4 hours post-treatment, respectively. In the multiple dose experiments, mice were dosed twice a day for 3 days and given an additional dose on Day 4. In addition, the mice were placed in the glass cylinders containing water at 25 degrees Celsius and allowed to swim for six minutes on Day 3. Statistical evaluation was performed using a computer program based on probit analysis. Statistical significance was determined using Student's t-test at a P value of <0.05.

(Results)

The test compound, administered in a single dose, to mice reduced mean duration of immobility in a dose-dependent manner for doses of 10, 15 and 30 mg/kg PO. 10 mg/kg of the test compound reduced the mean duration of immobility to 101 sec compared to 131 sec for control. Doses of 15 and 30 mg/kg produced significant reductions of mean immobility time from 154 sec to 80 sec and from 132 sec to 30 sec, respectively. The ED50 value (50% reduction in mean immobility time) for the test compound was 16.6 mg/kg.

The test compound, after multiple dosing, to mice reduced mean duration of immobility in a dose-dependent manner for doses of 3, 5 and 8 mg/kg PO. At 3 mg/kg of test compound, mean duration of immobility was reduced to 63 sec from 85 sec for control. Doses of 5 and 8 mg/kg produced significant reductions of mean immobility time from 136 sec to 73 sec and from 114 sec to 39 sec, respectively. The ED50 value for the test compound was 5.5 mg/kg PO.

In rats, the test compound administered at 30 mg/kg significantly reduced mean duration of immobility from 38 sec to 9 sec at 4 hours post-treatment. Doses of test compound at 10 and 15 mg/kg also reduced duration of immobility from 74 sec to 62 sec and 65 sec to 39 sec, respectively, but these differences were not statistically significant. The ED50 was 18.5 mg/kg PO which is similar to the ED50 value in mice above.

REFERENCES CITED

All references cited herein are incorporated herein by reference in their entirety and for all purposes to the same extent as if each individual publication or patent or patent application was specifically and individually indicated to be incorporated by reference in its entirety for all purposes.

The discussion of references herein is intended merely to summarize the assertions made by their authors and no admission is made that any reference constitutes prior art. Applicants reserve the right to challenge the accuracy and pertinence of the cited references.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein will be apparent to those skilled in the art from the foregoing description. Such modifications and variations are intended to fall within the scope of the appended claims. The present invention is to be limited only by the terms of the appended claims, along with the full scope of equivalents to which such claims are entitled.

The invention claimed is:

1. A method of treating fibromyalgia syndrome, comprising administering a therapeutically effective amount of a compound having structural Formula (1) or a pharmaceutically acceptable salt thereof, to a mammal suffering from fibromyalgia syndrome and in need of treatment:

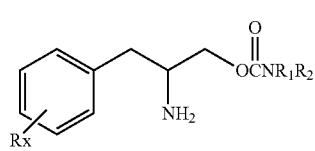

(1)

wherein,

R is selected from the group consisting of hydrogen and lower alkyl of 1 to 8 carbon atoms, halogen selected from F, Cl, Br and I, alkoxy of 1 to 3 carbon atoms, nitro group, hydroxy, trifluoromethyl, and thioalkoxy of 1 to 3 carbon atoms;

x is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl, arylalkyl, and cycloalkyl of 3 to 7 carbon atoms; or $R_1$ and $R_2$ can be joined to form a 5 to 7-membered heterocycle substituted with a member selected from the group consisting of hydrogen, alkyl, and aryl groups, wherein the heterocyclic compound comprises 1 to 2 nitrogen atoms and 0 to 1 oxygen atom, and the nitrogen atoms are not directly connected with each other or with the oxygen atom.

2. The method of claim 1, wherein the compound having structural Formula (1) is an enantiomer substantially free of other enantiomers or an enantiomeric mixture wherein one enantiomer of the compound having structural Formula (1) predominates.

3. The method of claim 2, wherein one enantiomer predominates to the extent of about 90% or greater.

4. The method of claim 3, wherein one enantiomer predominates to the extent of about 98% or greater.

5. The method of claim 2, wherein the enantiomer is (S) or (L) enantiomer as represented by Structural Formula (1a):

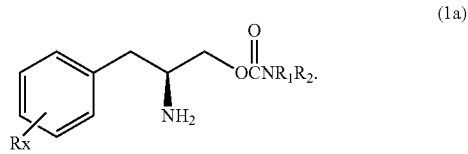

(1a)

6. The method of claim 5, wherein one enantiomer predominates to the extent of about 90% or greater.

7. The method of claim 6, wherein one enantiomer predominates to the extent of about 98% or greater.

8. The method of claim 2, wherein the enantiomer is (R) or (D) enantiomer, as represented by Structural Formula (1b):

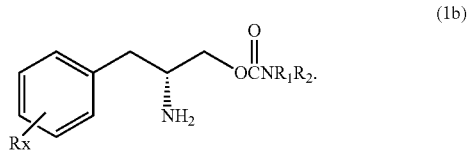

(1b)

9. The method of claim 8, wherein one enantiomer predominates to the extent of about 90% or greater.

10. The method of claim 9, wherein one enantiomer predominates to the extent of about 98% or greater.

11. The method of claim 1, wherein $R_1$ and $R_2$ can be the same or different from each other and are independently selected from the group consisting of hydrogen, lower alkyl of 1 to 8 carbon atoms, phenyl, phenyl-methylenyl, or cycloalkyl of 3 to 7 carbon atoms.

* * * * *